US006387943B1

(12) United States Patent
Ramakrishna et al.

(10) Patent No.: US 6,387,943 B1
(45) Date of Patent: May 14, 2002

(54) VANCORESMYCIN, A PROCESS FOR ITS PRODUCTION AND ITS USE AS A PHARMACEUTICAL

(75) Inventors: Nirogi Venkata Satya Ramakrishna; Ravi Gajanan Bhat, both of Mumbai; Eyyammadichiyil Sankaranarayanan Sreekumar, Maharashtra; Erra Koteswara Satya Vijayakumar; Shantilal Dayaram Naker, both of Mumbai; Uttara Vinayak Oak; Rajendra Prakash Tanpure, both of Maharashtra, all of (IN); Cordula Hopmann, Frankfurt am Main (DE); Michael Kurz, Hofheim (DE); Joachim Wink, Rödermark (DE); Gerhard Seibert, Darmstadt (DE); Dominique Le Beller, Jaux; Jozsef Aszodi, Pontault Combault, both of (FR)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/436,718

(22) Filed: Nov. 9, 1999

(30) Foreign Application Priority Data

Nov. 9, 1998 (EP) ............................................. 98121299

(51) Int. Cl.$^7$ ........................ A61K 31/40; C07D 405/12
(52) U.S. Cl. ........................ 514/422; 514/423; 514/425; 514/428; 548/517
(58) Field of Search ................... 514/422, 423, 514/425, 428; 548/517

(56) References Cited

FOREIGN PATENT DOCUMENTS

| EP | 0 818 539 A1 | 1/1998 |
| JP | 5-163289 | 6/1993 |

OTHER PUBLICATIONS

The American Heritage Dictionary, Second College Edition, 1982, pp. 1172, 1202.*
Kuniyoshi Tanaka et al., "Structure–Activity Relationships in Tetronic Acids and Their Copper(II) Complexes," Chem. Pharm. Bull., vol. 27, pp. 1901–1906 (1979).
Keizo Matsuo et al., "Structure–Activity Relationships in Tetramic Acids and Their Copper (II) Complexes," Chem. Pharm. Bull., vol. 28, pp. 2494–2502 (1980).
Mitsuhiro Ueno et al., "Dethymicin, A Novel Immunosuppressant Isolated From An *Amycolatopis*," The Journal of Antibiotics, vol. 45, No. 12, pp. 1819–1826 (1992).

* cited by examiner

Primary Examiner—Floyd D. Higel
Assistant Examiner—Ebenezer Sackey
(74) Attorney, Agent, or Firm—Finnegan, Henderson, Farabow, Garrett & Dunner, L.L.P.

(57) ABSTRACT

The present invention relates to a compound named Vancoresmycin which is obtainable by cultivation of the microorganism HIL-006734 (DSM 12216), and to its pharmaceutically acceptable salts. The present invention further relates to a process for the production of Vancoresmycin, to the microorganism HIL-006734 (DSM 12216), to the use of Vancoresmycin and its pharmaceutically acceptable salts as pharmaceuticals, and in particular to their use as antibiotics, and to pharmaceutical compositions comprising Vancoresmycin or a pharmaceutically acceptable salt thereof.

18 Claims, 3 Drawing Sheets

VANCORESMYCIN, A PROCESS FOR ITS PRODUCTION AND ITS USE AS A PHARMACEUTICAL

Under the provisions of Section 119 of 35 U.S.C., Applicants hereby claim the benefit of the filing date of European Patent Application Number 98121299.6, filed Nov. 9, 1998.

FIELD OF THE INVENTION

This invention relates to a compound named Vancoresmycin, which is obtainable by cultivation of the microorganism HIL-006734 (DSM 12216), and to its pharmaceutically acceptable salts and derivatives. The present invention further relates to a process for the production of Vancoresmycin, to the microorganism HIL-006734 (DSM 12216), to the use of Vancoresmycin and its pharmaceutically acceptable salts and derivatives as pharmaceuticals, including their use as antibiotics, and to pharmaceutical compositions comprising Vancoresmycin or a pharmaceutically acceptable salt or derivative thereof.

BACKGROUND OF THE INVENTION

Methicillin resistant *Staphylococcus aureus* (MRSA) infections are known to be predominant in several infectious conditions, for example, wounds and burns. Vancomycin and teicoplanin, belonging to the glycopeptide class, are the only two antibiotics clinically used for the treatment of MRSA infections. Due to the recent emergence of vancomycin- and teicoplanin-resistant strains, however, these infections are reported to have become menacing and fatal. In response, an intensive search for a structurally different class of compounds active against these vancomycin- and teicoplanin-resistant strains has been initiated. For instance, methylsulfomycin I, a cyclic thiopeptide, has been described earlier (European Patent Publication No. 0818539 filed Jul. 11, 1996) as an antibiotic active against vancomycin- and teicoplanin-resistant strains.

It has now been found that a novel compound named Vancoresmycin has antibiotic activity.

DETAILED DESCRIPTION OF THE INVENTION

The present invention relates to Vancoresmycin, a compound of the formula:

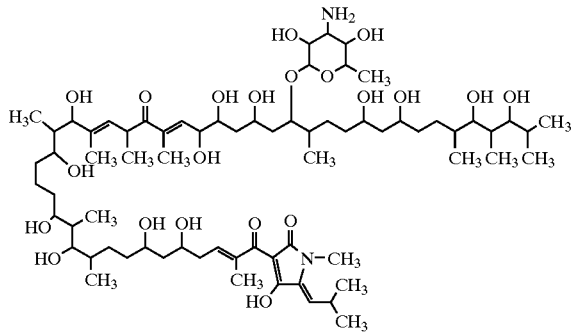

and to its pharmaceutically acceptable salts and derivatives, such as esters, ethers, and obvious chemical equivalents, including all stereoisomeric forms and all tautomeric forms.

Vancoresmycin has the molecular formula $C_{71}H_{126}N_2O_{21}$ (MW1343.80) and may be characterized by any one or more of its physico-chemical and spectral properties given below, such as its $^1$H NMR spectroscopic data and its $^{13}$C NMR spectroscopic data, both provided in Table 2.

Vancoresmycin is a new antibiotic active against vancomycin- and teicoplanin-resistant strains. It has a hitherto unreported structure with a tetramic acid moiety bearing an acyl substituent at the 3-position. This acyl substituent has a highly oxygenated long alkyl chain substituted with an amino sugar. A chemical abstract literature search established Vancoresmycin to be a new compound.

Vancoresmycin may be obtained by cultivating a microorganism referred to as culture No. HIL-006734 (henceforth referred to as HIL-006734). This microorganism was isolated from a soil sample collected from National Park, Borivli, Mumbai, India. The microorganism HIL-006734 belongs to the order of Actinomycetalos, genus Amycolatopsis. It was deposited on Jun. 4, 1998 with the German Collection of Microorganisms and Cell Cultures (DSMZ—Deutsche Sammlung von Mikroorganismen und Zelikulturen GmbH), Braunschweig, Germany, and has been given the accession number DSM No. 12216.

The present invention further provides a process for the production of Vancoresmycin from Amycolatopsis species HIL-006734, its mutants and variants, comprising the steps of: growing the Amycolatopsis species HIL-006734 under aerobic conditions in a nutrient medium containing one or more sources of carbon and one or more sources of nitrogen and optionally nutrient inorganic salts and/or trace elements; isolating the Vancoresmycin compound; and purifying the Vancoresmycin compound in a customary manner.

Mutants and variants of the microorganism HIL-006734 may also be able to synthesize the compound according to the present invention. Such mutants may be produced in a known manner by physical means, for example irradiation such as with ultraviolet- or X-rays, or chemical mutagens, such as ethylmethylansulfonate (EMS), 2-hydroxy4-methoxy-benzophenone (MOB) or N-methyl-N'-nitro-N-nitrosoguanidine (MNNG).

The screening for suitable mutants and variants which can produce the compound according to the invention can be confirmed by determination of the biological activity of the active compounds accumulated in the culture broth, for example by testing the antibacterial action.

The nutrient medium preferably contains sources of carbon, nitrogen and nutrient inorganic salts. The carbon sources are, for example, starch, glucose, sucrose, dextrin, fructose, molasses, glycerol, lactose, or galactose. A typical carbon source is starch. The sources of nitrogen are, for example, soybean meal, peanut meal, yeast extract, beef extract, peptone, malt extract, corn steep liquor, gelatin, casamion acids. Peptone and yeast extract are typical. The nutrient inorganic salts are, for example, sodium hydrogen phosphate, potassium hydrogen phosphate, sodium chloride, calcium chloride, calcium carbonate, potassium nitrate, ammonium sulphate, and magnesium sulphate. Calcium carbonate, sodium chloride, and magnesium sulphate are typical.

The cultivation of HIL-006734 may be carried out at temperatures between 25–35° C. and pH between 6.0 and 8.0. Typically, HIL-006734 is cultivated at 30° C. (±1° C.) and pH 7.0.

A good yield of the antibiotic of the invention may be obtained by cultivating HIL-006734 for 60–96 hours. Typically, cultivation is carried out by fermentation for 68–96 hours under submerged conditions, for example in shake flasks, as well as in laboratory fermenters. The progress of fermentation and formation of the Vancoresmycin can be detected by High Pressure Liquid Chromatography (HPLC) and by measuring the bioactivity of the culture broth against Staphylococci and Enterococci species by the known microbial agar plate diffusion assay method. The preferred culture is *Staphylococcus aureus* 3066, which is a resistant strain to methicillin, a pβlactam antibiotic reported in the literature, and *Entrococcus faecium* (*E. faecium* VR-1), which is resistant to vancomycin. In the resulting culture broth, Vancoresmycin is present in the culture filtrate as well as in mycelium and can be isolated using known separation techniques. Thus, it can be recovered from the culture filtrate by extraction at pH 5–8 with a water immiscible solvent such as ethyl acetate, dichloromethane, chloroform, or butanol, or by hydrophobic interaction chromatography using polymeric resins such as "Diaion HP-20®" (Mitsubishi Chemical Industries Limited, Japan), "Amberlite XAD®" (Rohm and Hass Industries U.S.A.) activated charcoal, or by ion exchange chromatography at pH 5–8. Typically, the active material is extracted with ethyl acetate. The active material can also be recovered from mycelium by extraction at pH 5–8 with a water miscible solvent such as methanol, acetone, acetonitrile, n-propanol, or iso-propanol. Alternatively, it may be extracted at pH 5–8 with a water immiscible solvent such as ethyl acetate, dichloromethane, chloroform, or butanol. Typically, the active material is extracted at pH 5–8 with ethyl acetate. Concentration and lyophilization of the extracts gives the active crude material.

The antibiotic Vancoresmycin of the present invention may, for example, be recovered from the crude material as follows:

By fractionation using any of the following techniques: normal phase chromatography (using alumina or silica gel as stationary phase; eluents such as petroleum ether, ethyl acetate, methylene chloride, acetone, chloroform, methanol, or combinations thereof; and additions of amines such as $NEt_3$); reverse phase chromatography (using reverse phase silica gel such as dimethyloctadecylsilylsilica gel, (RP-18) or dimethyloctylsilyl silica gel (RP-8) as stationary phase; and eluents such as water, buffers (for example, phosphate, acetate, citrate (pH 2–8)), and organic solvents (for example, methanol, is acetonitrile, acetone, tetrahydrofuran, or combinations of these solvents)); gel permeation chromatography (using resins such as ®Sephadex LH-20 (Pharmacia Chemical Industries, Sweden), TSKgel ®Toyopearl HW (TosoHaas, Tosoh Corporation, Japan) in solvents such as methanol, chloroform, acetone, ethyl acetate, or their combinations, or ®Sephadex G-10 and G-25 in water); or by counter-current chromatography (using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is chromatography over reverse phase silica gel (RP-18).

The compound Vancoresmycin may be converted into pharmaceutically acceptable salts and derivatives, like esters and ethers, and other obvious chemical equivalents, which are all covered by the present invention. The salts and derivatives can be prepared by standard procedures known to one skilled in the art. Salts like sodium and potassium salts, for example, may be prepared by treating Vancoresmycin with suitable sodium or potassium bases.

Esters and ethers may be prepared by the methods given in the literature, for example, in Advanced Organic Synthesis, $4^{th}$ Edition, J. March, John Wiley & Sons., 1992.

The amino group of the sugar moiety can be alkylated or acetylated, e.g. with acid chlorides by standard procedures known to one skilled in the art.

Chemical equivalents may be stable complexes with metal ions, e.g. transition metals like $La^{3+}$, $Sm^{3+}$, $Eu^{3+}$, $Gd^{3+}$, which are typical for tetramic acid derivatives and may be prepared by the methods given in the literature (K. Tanaka et. al., *Chem. Pharm. Bull.* 1979, 27,1901; K. Matsuo, *Chem. Pharm. Bull.* 1980, 28, 2494).

The double bonds of the alkyl side chain may be reduced by the methods given in the literature, for example in P. N. Rylander, "Hydrogenation Methods", Academic Press, New York (1985), Chpt. 2, or may be hydrohalogenated by methods described by H. O. House in "Modern Synthetic Reactions", W. A. Benjymin, Inc., New York (1972), pp 446–452. Hydroxylated derivatives may be produced by reaction of the double bonds with reagents such as $OsO_4$ as described in the literature, e.g. in *Chem. Rev.* 1980, 80, 187.

Derivatives may also be formed by conversion of the double bonds into epoxides by oxidation, e.g. with MCPBA, as described in Advanced Organic Synthesis, $4^{th}$ Edition, J. March, John Wiley & Sons., 1992.

Vancoresmycin has antibacterial activity. Minimum inhibitory concentrations of Vancoresmycin against a wide range of bacterial are given in Table 3 below. Vancoresmycin and its pharmaceutically acceptable salts and derivatives can be administered to animals, such as mammals, including humans, as pharmaceuticals on their own, in mixtures with one another, and in the form of pharmaceutical compositions that permit parenteral administration. Accordingly, the present invention also relates to Vancoresmycin and its pharmaceutically acceptable salts and derivatives for use as pharmaceuticals and to the use of Vancoresmycin and its pharmaceutically acceptable salts and derivatives for the production of medicaments having antibacterial activity. The present invention further relates to pharmaceutical compositions which contain an effective amount of Vancoresmycin and/or one or more pharmaceutically acceptable salts and/or derivatives thereof, together with a pharmaceutically acceptable carrier.

Vancoresmycin can be administered orally, intramuscularly, intravenously, or by other modes of administration. Pharmaceutical compositions which contain Vancoresmycin or a pharmaceutically acceptable salt or derivative thereof with other pharmaceutically active substances can be prepared by mixing the active compounds with one or more pharmacologically tolerated auxiliaries and/or excipients such as, for example, fillers, emulsifiers, lubricants, masking flavors, colorants, or buffer substances, and converting the mixture into a suitable pharmaceutical form such as, for example, tablets, coated tablets, capsules, granules, powders, emulsions, suspensions, or solutions suitable for parenteral administration.

Examples of auxiliaries and/or excipients which may be mentioned are tragacanth, lactose, talc, agar—agar, polyglycols, ethanol, and water. Suitable and preferred for parenteral administration are suspensions or solutions in water. It is also possible to administer the active substances as such, without vehicles or diluents, in a suitable form, for example, in capsules.

As is customary, the galenic formulation and the method of administration as well as the dosage range which are suitable in a specific case depend on the species to be treated and on the state of the respective condition or disease, and can be optimized using methods known in the art. On average, the daily dose of active compound in a patient of about 75 kg weight is at least 0.001 mg to at most 10 mg, typically at most 10 mg.

Figure 1:
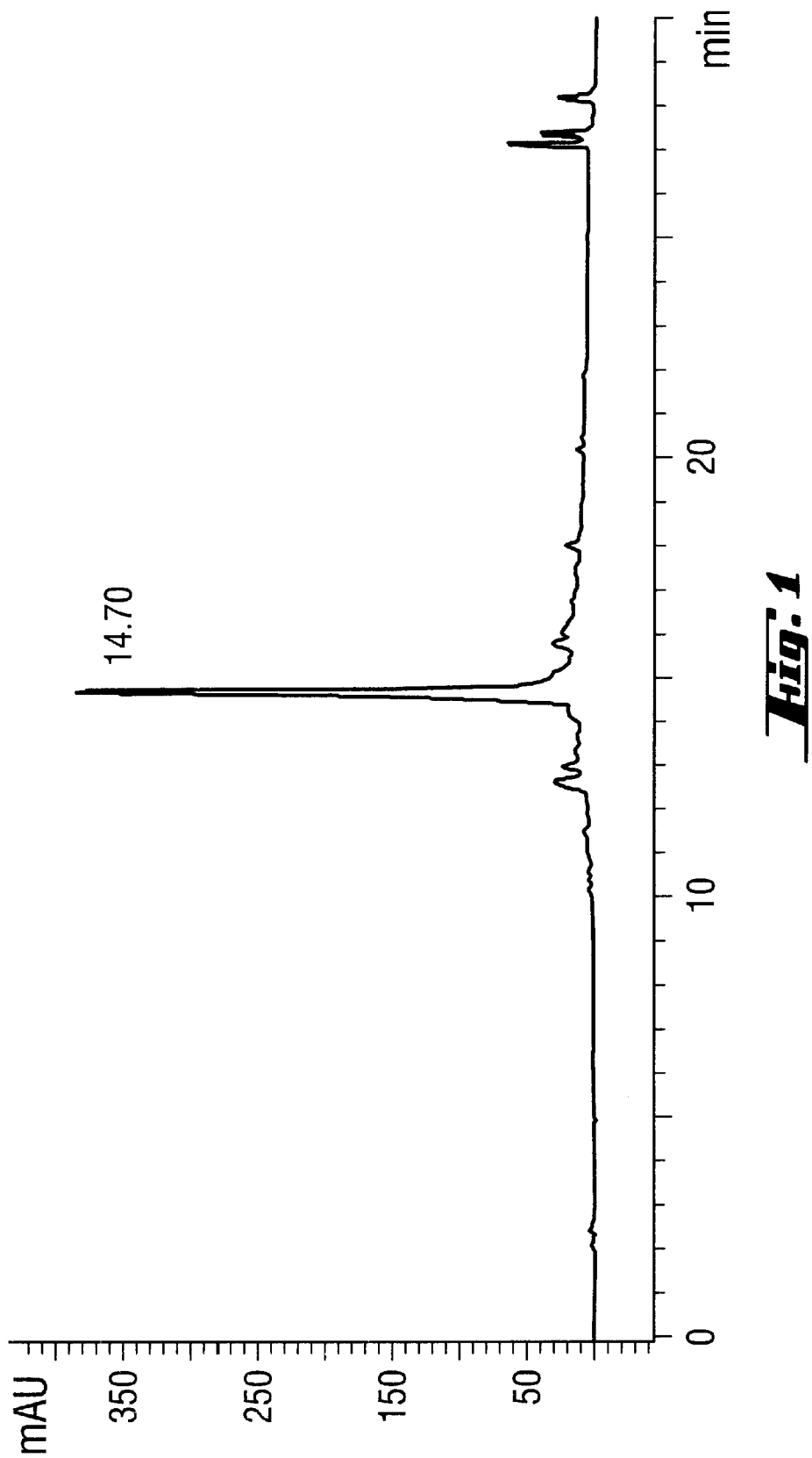
FIG. 1 Preparative HPLC chromatogram from the purification of Vancoresmycin. See Table 1.

The following are provided as illustrative examples of the present invention and do not limit the scope thereof:

EXAMPLE 1

Isolation of the Culture No. HIL-006734 from Soil a) Composition of Nutrient Isolation Medium

| | |
|---|---|
| Corn starch | 10.0 g |
| Casein | 1.0 g |
| Peptone | 1.0 g |
| Beef extract | 1.0 g |
| $K_2HPO_4$ | 0.5 g |
| Agar powder | 13.0 g |
| Demineralized water | 1.0 liter |
| pH | 7.5 | b) Soil Plating and Isolation 10 g of soil collected from National Park, Borivii, Mumbai, India were added to 90 ml of sterilized water in a 250 ml Erlenmeyer flask which was shaken for 2 hours on a rotary shaker (220 rpm). The above soil suspension was serially diluted in steps of 10 up to $10^{-5}$. From the last dilution, 1 ml of suspension was placed at the center of a sterile glass petri plate (15 cm diameter) to which was poured approximately 50 ml of the above isolation medium supplemented with 25 µg/ml of amphotericin B as antifungal agent and cooled to 45° C. and the plate swirled thoroughly. The mixture of soil suspension and medium was allowed to settle and incubated at 28° C. (±1° C.) for 7 days. The petri plate was periodically observed and HIL-006734 (culture No. Y-9439786) was isolated from amongst the growing microorganisms.

EXAMPLE 2

Maintenance of the Culture No. HIL-006734

Composition of Maintenance Medium

HIL-006734 was maintained on the following medium:

| | |
|---|---|
| Malt extract | 10.0 g |
| Glucose | 4.0 g |
| Yeast extract | 4.0 g |
| Actidiol | 0.05 g |
| Agar powder | 13.0 g |
| Demineralized water | 1 liter |
| pH | 7.0–7.5 |

After dissolving the ingredients thoroughly by heating, the resultant solution was distributed in test tubes and sterilized at 121° C. for 20 min. The test tubes were cooled and allowed to solidify in a slanting position. The agar slants were streaked with the growth of HIL-006734 by a wire loop and incubated at 28° C. (±1° C.) until a good growth was observed. The well-grown cultures were stored in the refrigerator at +8° C.

Preparation of Glycerol Working Seed

Composition of Medium

| | |
|---|---|
| Yeast extract | 4.0 g |
| Soluble starch | 15.0 g |
| $K_2HPO_4$ | 1.0 g |
| $MgSO_4 \times 7 H_2O$ | 0.5 g |
| Demineralized water | 1 liter |
| PH | 7.0 |

The above medium was distributed in 100 ml amounts in 300 ml Erlenmeyer flasks and autoclaved at 121° C. for 20 minutes. The flasks were cooled to room temperature and inoculated with the abovementioned agar slant. The incubation was carried out for five days on a rotary shaker at 180 rpm and 28° C. 1.5 ml of this culture was mixed with 1.5 ml glycerol (99%) and stored at −20° C.

EXAMPLE 3

Fermentation of the Culture No. HIL-006734 in Shake Flasks

| Composition of seed medium | |
|---|---|
| Glucose | 15.9 g |
| Soybean meal | 15.0 g |
| Corn steep liquor | 5.0 g |
| $CaCO_3$ | 2.0 g |
| NaCl | 5.0 g |
| Demineralized water | 1 liter |
| pH | 6.8–7.0 |

The medium could be used with or without corn steep liquor.

The above medium was distributed in 100 ml amounts in 500 ml Erlenmeyer flasks and autoclaved for 20 mins. The flasks were cooled to room temperature and each flask was inoculated with a loopful of the above mentioned well-grown culture of Example 2 and shaken on a rotary shaker for 72 hours at 240 rpm at 27° C. (±1° C.) to give seed culture.

| Composition of production medium | |
|---|---|
| Glucose | 20.0 g |
| Soybean meal | 10.0 g |
| $CaCO_3$ | 0.2 g |
| $CoCl_2.6H_2O$ | 0.001 g |
| Demineralized water | 1 liter |
| pH | 6.8 |
| or | |
| Starch | 10.0 g |
| Glucose | 10.0 g |
| Glycerol 99% | 10.0 g |
| Corn steep liquor | 2.5 g |
| Peptone | 5.0 g |
| Yeast extract | 2.0 g |
| NaCl | 1.0 g |
| $CaCO_3$ | 3.0 g |
| Demineralized water | 1 liter |
| pH | 7.2 (before sterilization) |

The production medium was distributed in 100 ml amounts in 500 ml Erlenmeyer flasks and autoclaved at 121° C. for 20 min. The flasks were cooled to room temperature and inoculated with the abovementioned seed culture (2% v/v). The fermentation was carried out on a rotary shaker at 240 rpm and 27° C. (±1° C.) for 48 hours. The production of the antibiotic was determined by testing the bioactivity against *S. aureus* 3066 and *Ent. faecium* VR-1 using the well diffusion method in a known manner.

EXAMPLE 4

Cultivation of the Culture No. HIL-006734 in Fermenters

Preparation of Seed Culture in Shake Flasks

The seed medium of Example 3 was distributed in 150 ml amounts in 1000 ml Erlenmeyer flasks and autoclaved at 121° C. for 20 mins. The seed culture was grown in these flasks as described in Example 3.

Large Scale Fermentation

Composition of production medium:

| | |
|---|---|
| Glucose | 20.0 g |
| Soybean meal | 10.0 g |
| CaCO₃ | 0.2 g |
| CoCl₂.6H₂O | 0.001 g |
| Demineralized water | 1 liter |
| pH | 7.0 |
| or | |
| Starch | 10.0 g |
| Glucose | 10.0 g |
| Glycerol 99% | 10.0 g |
| Corn steep liquor | 2.5 g |
| Peptone | 5.0 g |
| Yeast extract | 2.0 g |
| NaCl | 1.0 g |
| CaCO₃ | 3.0 g |
| Demineralized water | 1 liter |
| pH | 7.2 (before sterilization) |

20 liters of the production medium in 22 liter fermenter (in two fermenters) and 9 liters of the production medium in 12 liter fermenter (in two fermenters) along with 1 ml(/10 liter fermenter) of ®Desmophen as antifoaming agent was sterilized in situ for 40 mins. at 121° C., cooled to 27° C. (±1°C.) and seeded with 1.5 liter(/22 liter fermenter) or 0.75 liter (/12 liter fermenter) of the seed culture mentioned above.

The fermentation was run with the following parameters:

| | |
|---|---|
| Temperature | 27° C. (±1° C.) |
| Agitation | 200 rpm |
| Aeration | 15 lpm/22 liter fermenter |
| | 10 lpm/12 liter fermenter |
| Harvest time | 64 hours |

The production of the antibiotic was determined by testing the bioactivity against *S. aureus* 3066 and *Ent. faecium* VR-1 and HPLC analysis. The final pH of the culture broth was 7.0–7.5. The culture broth was harvested and centrifuged and the antibiotic was isolated and purified from the culture filtrate and the mycelium by the method described in the Example 5 or 6.

EXAMPLE 5

Isolation and Purification of Vancoresmycin

The culture broth (60 liters) was harvested and centrifuged to separate the mycelium (2.5 kg) and culture filtrate (50 liters, pH 7.3). The mycelium was extracted with methanol (2×20 liters) and the active extracts were pooled and concentrated under reduced pressure to get 70 g of crude material. The culture filtrate (50 liters, pH 7.3) was adjusted to pH 5.5 with 2N hydrochloric acid and passed through a column of ®Diaion HP-20 (2.5 liters). The column was washed with water (10 liters) followed by 15 liters of methanol:water (1:1). The active compound was found to be present in 15 liters of methanol:water (3:1) and 30 liters methanol eluates. The monitoring of the purification was done by bioassay against *S. aureus* 3066 and *Ent. faecium* VR-1. The active eluates were pooled and concentrated to get 15 g of crude material. The combined crude was chromatographed on ®Sephadex LH-20 column (2.5 cm×90 cm) in methanol repeatedly and the active fractions were pooled and concentrated. This was further chromatographed on ®Toyopearl TSK HW 40F column (6 cm×35 cm) in methanol. The active fractions were pooled and concentrated under reduced pressure to get 3 g of semipure material. The final purification was done by preparative HPLC using the following conditions:

The semi-pure material was finally purified by preparative HPLC on a 25 mm×250 mm Hibar -Lichrospher RP-18 (10μ using 67.5:32.5 Methanol: Phosphate buffer (0.01M, pH 6.5) as the eluant at a flow rate of 23 ml/min and detection at 220 nm).

The active eluates were pooled and concentrated under reduced pressure to remove the solvent and then desalted on ®5Diaion HP-20 (50 ml) column, eluted with acetonitrile-:water (80:20) and concentrated under reduced pressure and lyophilized to get 70 mg of pure compound.

EXAMPLE 6

Isolation and Purification of Vancoresmycin

The culture broth (200 liters) was harvested and centrifuged to separate the mycelium and the culture filtrate. The mycelium was exhaustively extracted with methanol (30–40 L) and the extract concentrated 1:10 to obtain a colorless precipitation which was filtered off to obtain 30–50 g of crude material. This material was further purified by HPLC:

1.) Column: Fractogel TSK-HW 40 (4 L, 500×100 mm)

Eluent: MeOH

Flow: 20 ml/min

Detection: 204 and 236 nm

The active fractions were eluted after 125 min. The pooled fractions were concentrated under reduced pressure and freeze dried.

2.) Column: Silica Gel 60 (Merck); Erimatech (300×20 mm, 100 ml)

Eluent: A) CH₂Cl₂:MeOH 9:1 B) CH₂Cl₂:MeOH 3:1+1% NEt₃ C)MeOH

| Gradient: | min | % A | % B | % C |
|---|---|---|---|---|
| | 0 | 100 | 0 | 0 |
| | 23 | 100 | 0 | 0 |
| | 24 | 0 | 100 | 0 |
| | 51 | 0 | 100 | 0 |
| | 52 | 0 | 0 | 100 |
| | 93 | 0 | 0 | 100 |

Flow Rate: 25 ml/min

Detection: 236 and 288 nm

The vancoresmycin-containing fractions eluted after 32 min. The pooled fractions were concentrated under reduced pressure and freeze dried. The yield of the two purification columns was 50%.

The physico-chemical and spectral properties of Vancoresmycin are given in Tables 1 and 2. The minimum inhibitory concentrations (MIC) against various bacteria are listed in Table 3.

TABLE 1

Figure 2:
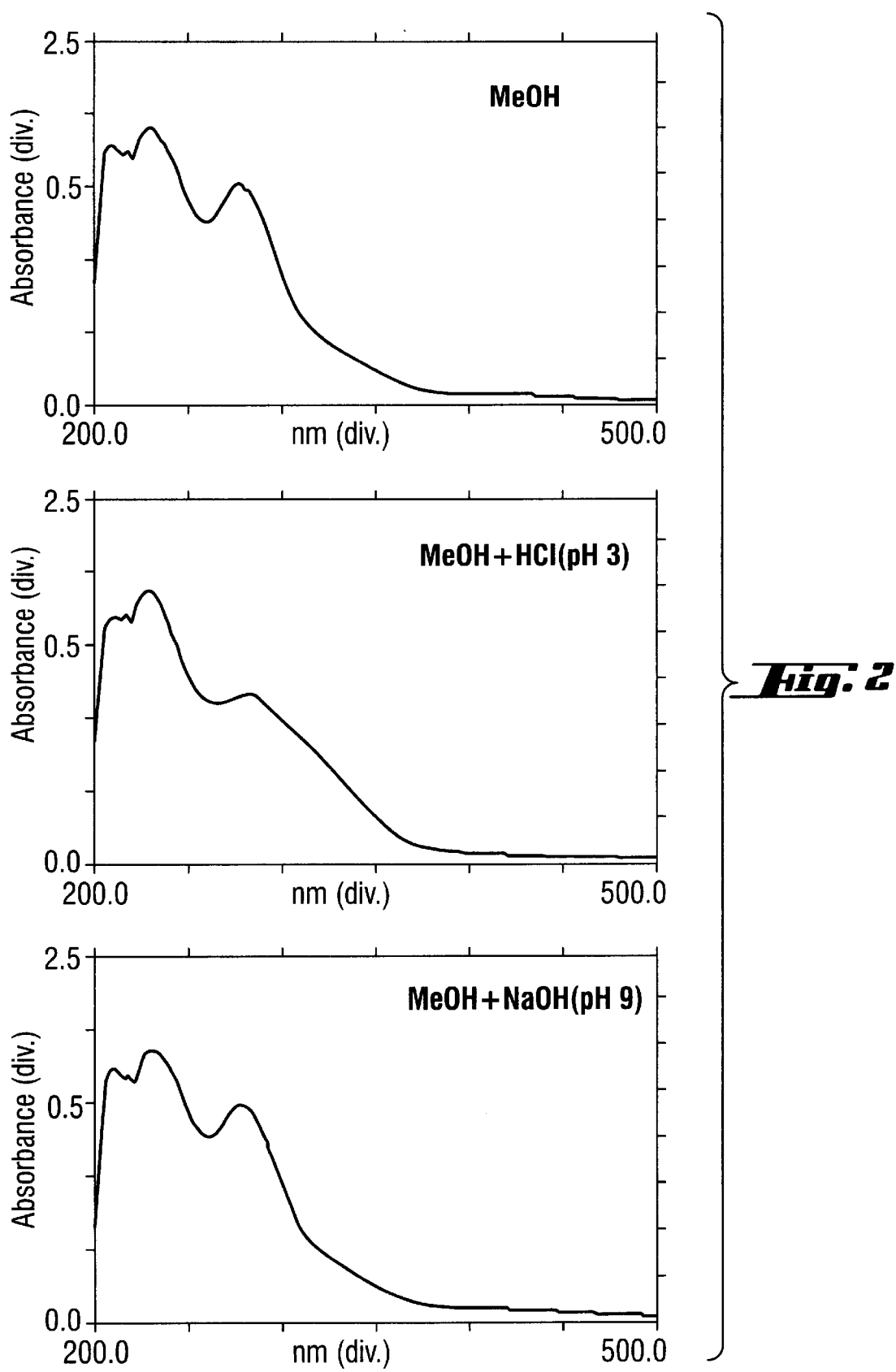
FIG. 2 UV spectra of Vancoresmycin, in different solvents. See Table 1.
Figure 3:
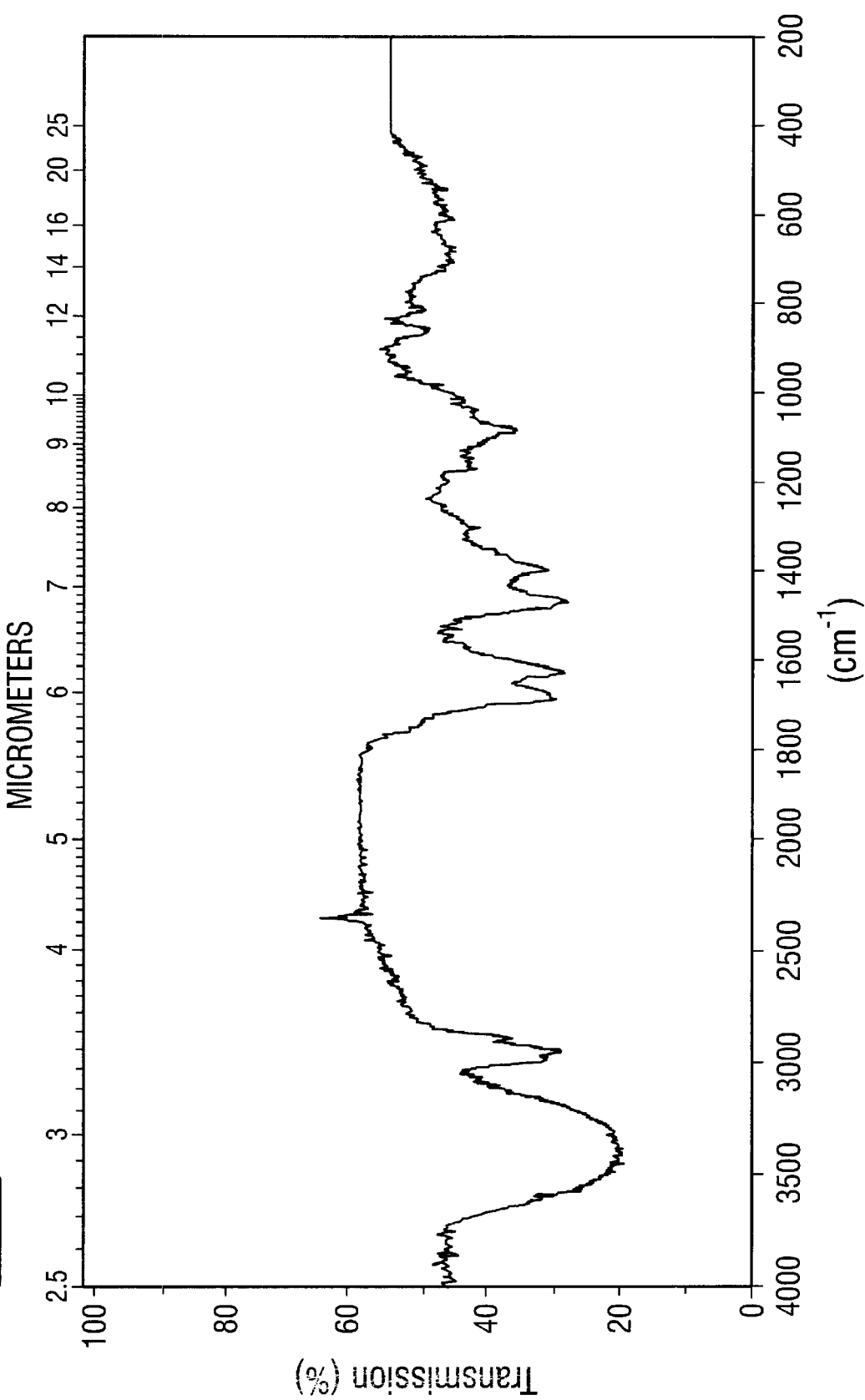
FIG. 3 IR spectrum of Vancoresmycin. See Table 1.

| | |
|---|---|
| Appearance: | White solid |
| Solubility: | Methanol, DMSO |
| Melting point: | 141–143° C. |
| $[\alpha]_D$: | −13° (c 0.2, Methanol) |
| TLC (Thin Layer: Chromatography) | Rf: 0.6 [Silica gel plate (Article No. 5554, E. Merck); n-BuOH:MeOH:water (4:1:2)] |
| HPLC (High Pressure: Liquid Chromatography) | Retention time: 14.70 min [Column: LiChrocart (250 mm × 4 mm) RP Select B (5μ; Eluant: Gradient of 0.1% aqueous orthophospharic acid (pH 2.5) to $CH_3CN$ in 20 min; Flow rate: 1 ml/min; Detection: 220 nm] FIG. 1 of the accompanying drawings |
| or: Column: | Purospher Star RP.18e (Merck), 55 × 4 mm, 3 μm |
| Eluent: | $CH_3CN/0.01\% H_3PO_4$ (85%) |
| Gradient: | time    % $CH_3CN$ |
| | 0.00    5.0 |
| | 3.00    95.0 |
| | 5.00    95.0 |
| | 6.00    5.0 |
| | 10.00   5.0 |
| Flow: | 2 ml/min |
| Temp.: | 40° C. |
| Detection: | 210 nm, 254, 280, 320, 380 |
| $t_R$: | 2.19 min |
| ESI-MS (Electrospray: Ionisation Mass) | 1342 (M − H)⁻ |
| HR-FAB-MS (High: resolution Fast Atom Bombardment Mass) | 1343.89142 (M + H)⁺ [Calculated for $C_{71}H_{127}N_2O_{21}$: 1343.889915 (M + H)⁺] |
| Mol. formula: | $C_{71}H_{126}N_2O_{21}$ |
| UV/VIS: | MeOH, $\lambda_{max}$ (logε) = 234 nm (4.39), 280 (4.29) (FIG. 2) |
| IR: | KBr, ν = 3384 cm⁻¹ (br), 2934 (m), 1674 (m), 1616 (s), 1456 (s), 1381 (m), 1064 (FIG. 3) |
| ¹H NMR: | see Table 2 |
| ¹³C NMR: | see Table 2 |

TABLE 2

¹H and ¹³C NMR Spectroscopic Data of Vancoresmycin in MeOD at 300 K.

| | ¹H | ¹³C |
|---|---|---|
| 1 | 0.85 | 14.76 |
| 2 | 0.97 | 20.83 |
| 3 | 1.86 | 31.20 |
| 4 | 3.40 | 82.19 |
| 5 | 1.69 | 39.54 |
| 6 | 0.77 | 13.64 |
| 7 | 3.53 | 80.19 |
| 8 | 1.65 | 36.40 |
| 9 | 0.86 | 12.75 |
| 10 | 1.43 | 31.20 |
| 11 | 1.43 | 36.52 |
| 12 | 3.74 | 72.03 |
| 13 | 1.60/1.54 | 44.90 |
| 14 | 3.75 | 72.03 |
| 15 | 1.57/1.38 | 36.61 |
| 16 | 1.49/1.16 | 30.18 |
| 17 | 1.94 | 38.60 |
| 18 | 0.92 | 15.04 |
| 19 | 3.86 | 81.67 |
| 20 | 4.59 | 103.48 |
| 21 | 3.83 | 72.03 |
| 22 | 2.48 | 57.61 |
| 23 | — | — |
| 24 | 3.08 | 75.08 |
| 25 | 3.21 | 74.66 |
| 26 | 1.27 | 18.29 |
| 27 | 1.52/1.42 | 39.35 |
| 28 | 3.96 | 65.82 |
| 29 | 1.49 | 42.39 |
| 30 | 3.79 | 72.47 |
| 31 | 4.31 | 73.26 |
| 32 | 6.61 | 142.09 |
| 33 | — | 138.52 |
| 34 | 1.82 | 12.75 |
| 35 | — | 206.04 |
| 36 | 4.20 | 41.01 |
| 37 | 1.14 | 17.77 |
| 38 | 5.36 | 128.35 |
| 39 | — | 138.72 |
| 40 | 1.67 | 12.75 |
| 41 | 3.98 | 80.53 |
| 42 | 1.63 | 41.30 |
| 43 | 0.88 | 8.10 |
| 44 | 3.58 | 73.85 |
| 45 | 1.48 | 36.52 |
| 46 | 1.62/1.32 | 23.51 |
| 47 | 1.55/1.32 | 33.36 |
| 48 | 3.79 | 75.08 |
| 49 | 1.73 | 42.71 |
| 50 | 0.77 | 11.91 |
| 51 | 3.40 | 77.82 |
| 52 | 1.61 | 36.28 |
| 53 | 0.85 | 12.70 |
| 54 | 1.54/1.33 | 31.34 |
| 55 | 1.61/1.44 | 36.28 |
| 56 | 3.77 | 71.83 |
| 57 | 1.67/1.62 | 44.53 |
| 58 | 3.90 | 71.28 |
| 59 | 2.29 | 37.53 |
| 60 | 5.75 | 129.78 |
| 61 | — | 141.66 |
| 62 | 1.82 | 13.98 |
| 63 | — | 195.36 |
| 64 | — | 174.52 |
| 65 | 3.22 | 27.78 |
| 66 | — | 136.51 |
| 67 | — | 183.80 |
| 68 | — | 100.31 |
| 69 | 5.35 | 116.05 |
| 70 | 3.07 | 26.50 |
| 71 | 1.09 | 24.46 |
| 72 | 1.09 | 24.46 |

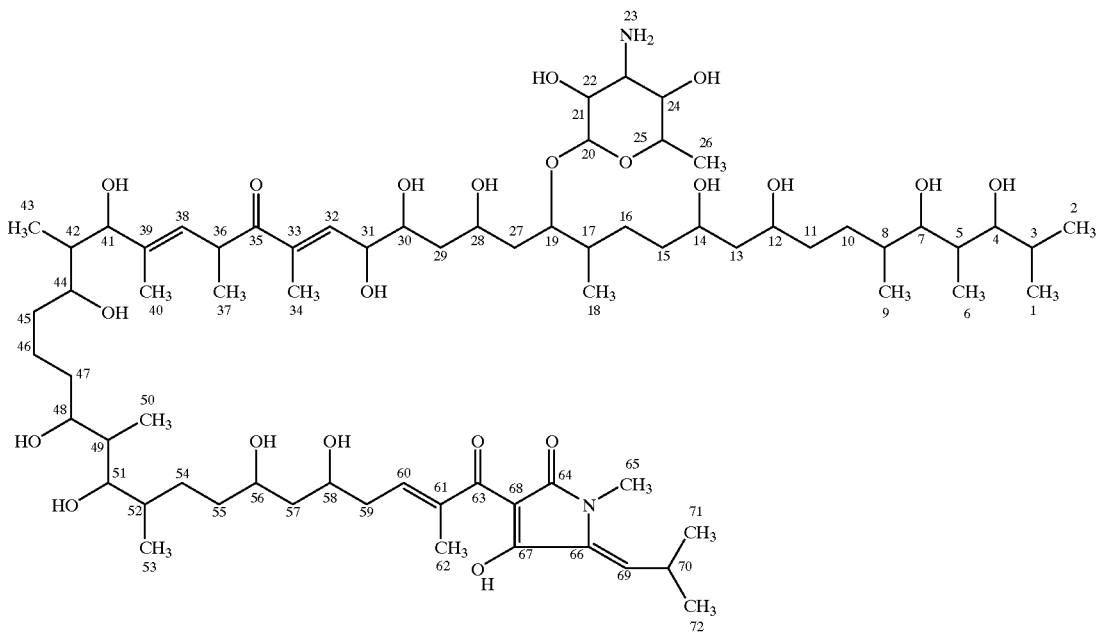

TABLE 3

| Test organism | MIC(μg/ml) |
| --- | --- |
| Staphylococcus aureus 209P | 0.05 |
| S. aureus 20240 | 0.05 |
| S. aureus E-710 | 0.10 |
| S. aureus SG511 | 0.05 |
| S. aureus 3066 | 0.10 |
| S. warneri 6563 II (2) | 0.10 |
| S. aureus E-712 | 0.10 |
| S. aureus 20424 | 0.10 |
| S. aureus Chantot 31153 | 0.05 |
| S. aureus Wein 11 | 0.05 |
| S. aureus Wein 12 | 0.05 |
| S. aureus 503(Mers) | 0.025 |
| S. aureus Brussel 4115 | 0.05 |
| S. aureus MLS-16 | 0.39 |
| S. haemolyticus 809 | 0.05 |
| S. epidermidis 825 | 0.10 |
| S. epidermidis 823 | 0.20 |
| S. epidermidis 607 | 0.10 |
| S. epidermidis 5747 IW | 0.10 |
| Enterococcus faecalis ATCC 29212 | 0.39 |
| Ent. faecalis D 21777 | 0.39 |
| Ent. faecalis D 23241 | 0.39 |
| Ent. faecalis D 756 | 0.39 |
| Ent. faecalis D 26777 | 0.39 |
| Ent. faecalis D 7F | 0.39 |
| Ent. faecium D-65 | 0.39 |
| Ent. faecium 5601 (H) | 0.39 |
| Ent. faecium P-1 | 0.39 |
| Ent. faecium P-2 | 0.39 |
| Ent. faecium VR-1 | 0.39 |
| Ent. hirae 55 | 0.39 |
| Ent. durans 4939H | 0.39 |
| Escherichia coli 9632 | >100 |
| E. coli super sen. 2231 | >100 |
| Pseudomonas aeruginosa M35 | >100 |

The present invention may be embodied in other specific forms without departing from its spirit or essential characteristics. The described embodiments are to be considered in all respects as illustrative only and not restrictive.

We claim:

1. Vancoresmycin, a compound of the formula:

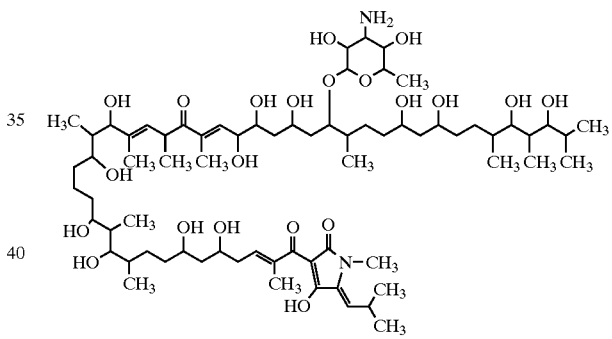

or a pharmaceutically acceptable salt of Vancoresmycin, a derivative of Vancoresmycin, a stereoisomer of Vancoresmycin, a stereoisomer of a pharmaceutically acceptable salt of Vancoresmycin, a stereoisomer of a derivative of Vancoresmycin, a tautomer of Vancoresmycin, a tautomer of a pharmaceutically acceptable salt of Vancoresmycin, or a tautomer of a derivative of Vancoresmycin.

2. Vancoresmycin, a compound of the molecular formula $C_{71}H_{126}N_2O_{21}$, obtained by cultivation of the microorganism Amycolatopsis strain HIL-006734 (DSM 12216), or a mutant thereof which produces Vancoresmycin, under aerobic conditions in a nutrient medium containing sources of carbon and nitrogen, followed by isolation, and purification, or a pharmaceutically acceptable salt of Vancoresmycin, a derivative of Vancoresmycin, a stereoisomer of Vancoresmycin, a stereoisomer of a pharmaceutically acceptable salt of Vancoresmycin, a stereoisomer of a derivative of Vancoresmycin, a tautomer of Vancoresmycin, a tautomer of a pharmaceutically acceptable salt of Vancoresmycin, or a tautomer of a derivative of Vancoresmycin.

3. A process for the production of a compound as claimed in claim 1 comprising the steps of:

cultivating the microorganism Amycolatopsis species HIL-006734 (DSM 12216) or one of its variants or mutants under aerobic conditions in a nutrient medium containing sources of carbon and nitrogen to produce Vancoresmycin, isolating the Vancoresmycin, and purifying the Vancoresmycin.

4. A process for the production of a compound as claimed in claim 2 comprising the steps of:

cultivating the microorganism Amycolatopsis species HIL-006734 (DSM 12216) or one of its variants or mutants under aerobic conditions in a nutrient medium containing sources of carbon and nitrogen to produce Vancoresmycin, isolating the Vancoresmycin, and purifying the Vancoresmycin.

5. A process as claimed in claim 3, further comprising the step of reacting the Vancoresmycin with a suitable agent to form a pharmaceutically acceptable salt or derivative.

6. A process as claimed in claim 4, further comprising the step of reacting the Vancoresmycin with a suitable agent to form a pharmaceutically acceptable salt or derivative.

7. A pharmaceutical composition, comprising an effective amount of Vancoresmycin or a pharmaceutically acceptable salt or derivative thereof as claimed in claim 1 and a pharmaceutically acceptable carrier.

8. A pharmaceutical composition, comprising an effective amount of Vancoresmycin or a pharmaceutically acceptable salt or derivative thereof as claimed in claim 2 and a pharmaceutically acceptable carrier.

9. A method of treating an infection comprising administering to a patient in need thereof an effective amount of a compound as claimed in claim 1.

10. A method of treating an infection comprising administering to a patient in need thereof an effective amount of a compound as claimed in claim 2.

11. A method of treating a *Staphylococcus aureus* infection comprising administering to a patient in need thereof an effective amount of a compound as claimed in claim 1.

12. A method of treating a *Staphylococcus aureus* infection comprising administering to a patient in need thereof an effective amount of a compound as claimed in claim 2.

13. The method of claim 12, wherein the *Staphylococcus aureus* is vancomycin-resistant, teicoplanin-resistant, or vancomycin- and teicoplanin-resistant.

14. The method of claim 13, wherein the *Staphylococcus aureus* is vancomycin-resistant, teicoplanin-resistant, or vancomycin- and teicoplanin-resistant.

15. The method of claim 9, wherein the infecting organism is a Staphylococcus.

16. The method of claim 10, wherein the infecting organism is a Staphylococcus.

17. The method of claim 9, wherein the infecting organism is an Enterococcus.

18. The method of claim 10, wherein the infecting organism is an Enterococcus.

* * * * *

UNITED STATES PATENT AND TRADEMARK OFFICE
CERTIFICATE OF CORRECTION

PATENT NO. : 6,387,943 B1
DATED : May 14, 2002
INVENTOR(S) : Ramakrishna et al.

It is certified that error appears in the above-identified patent and that said Letters Patent is hereby corrected as shown below:

Column 13,
Line 3, "species" should read -- strain --.
Line 4, delete "variants or".
Line 12, "species" should read -- strain --.
Line 13, delete "variants or".

Signed and Sealed this

Fifth Day of November, 2002

Attest:

Attesting Officer

JAMES E. ROGAN
*Director of the United States Patent and Trademark Office*